US007011860B1

(12) United States Patent
Wakabayashi et al.

(10) Patent No.: US 7,011,860 B1
(45) Date of Patent: Mar. 14, 2006

(54) FLAVOR PRECURSOR COMPOSITION AND METHOD FOR RELEASING THE FLAVOR COMPONENT

(75) Inventors: Hidehiko Wakabayashi, Kawasaki (JP); Hirokazu Kawaguchi, Kawasaki (JP); Kyousuke Ishiguro, deceased, late of Kawasaki (JP); by Minori Ishiguro, legal representative, Yokohama (JP); by Tatsuya Ishiguro, legal representative, Tokyo (JP); by Shouji Ishiguro, legal representative, Yokohama (JP); by Youhei Ishiguro, legal representative, Hachioji (JP); Yoichi Ueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/926,180

(22) PCT Filed: Apr. 4, 2000

(86) PCT No.: PCT/JP00/02179

§ 371 (c)(1),
(2), (4) Date: Oct. 10, 2001

(87) PCT Pub. No.: WO00/63328

PCT Pub. Date: Oct. 26, 2000

(30) Foreign Application Priority Data

Apr. 20, 1999 (JP) ................................. 11-111725
Apr. 20, 1999 (JP) ................................. 11-111728

(51) Int. Cl.
*A23L 1/22* (2006.01)

(52) U.S. Cl. ..................... 426/533; 426/534; 426/535; 426/650

(58) Field of Classification Search ................ 426/533, 426/534, 535, 650
See application file for complete search history.

(56) References Cited

U.S. PATENT DOCUMENTS

| | | | |
|---|---|---|---|
| 3,709,697 | A | 1/1973 | De Groot et al. |
| 4,031,256 | A | 6/1977 | Evers et al. |
| 4,041,186 | A | 8/1977 | Evers et al. |
| 4,161,550 | A | 7/1979 | Bernhardt et al. |
| 4,889,736 | A | 12/1989 | Doornbos et al. |

FOREIGN PATENT DOCUMENTS

| | | |
|---|---|---|
| CH | 529 516 | 10/1972 |
| EP | 482 766 | 4/1992 |
| EP | 591 763 | 4/1994 |
| EP | 770 686 | 5/1997 |
| EP | 963 706 | 12/1999 |
| GB | 1 414 598 | 11/1975 |
| GB | 1 552 857 | 9/1979 |
| GB | 1 489 292 | 10/1997 |
| JP | 58-121286 | 7/1983 |
| JP | 58-183668 | 10/1983 |
| JP | 61-10506 | 1/1986 |
| JP | 1-101397 | 4/1989 |
| JP | 1-102506 | 4/1989 |
| JP | 5-230496 | 9/1993 |
| JP | 5-239491 | 9/1993 |
| JP | 5-255690 | 10/1993 |
| JP | 7-179328 | 7/1995 |
| JP | 8-188529 | 7/1996 |
| JP | 9-40687 | 2/1997 |
| JP | 9-108529 | 4/1997 |
| JP | 11-243904 | 9/1999 |
| JP | 2000-96078 | 4/2000 |
| WO | WO 96/14827 | 8/1996 |

OTHER PUBLICATIONS

G. P. Rizzi, Der. Food. Sci., vol. 37A, pp. 289-302, "Formation of Sulfur-Containing Flavor Compounds from Allylic Alcohol Precursors", 1995.
R. J. S. Hickman, et al., Aust. J. Chem., vol. 38, No. 6, pp. 899-904, "Synthesis of Aromatics-Substituted Derivatives of N-Acetyl-L-Cysteine", 1985.
L. J. Deterding, et al., Anal. Biochem., vol. 183, No. 1, pp. 94-107, "Fast Atom Bombardment and Tandem Mass Spectrometry for Structure Determination of Cysteine N-Acetylcysteine, and Glutathione Adducts of Xenobiotics", 1989.
R. J. S. Hickman, et al., Xenobiotica, vol. 22, No. 8, pp. 917-923, "Thioethers as Urinary Metabolites of Thiiophene and Monobromothiophenes", 1992.
L. J. Chen, et al., Chem. Res. Toxicol., vol. 10, No. 8, pp. 866-874, "Characterization of Amino Acid and Glutathione Adducts of CIS-2-Butene-1,4-Dial, A Reactive Metabolite of Furan", 1997.

*Primary Examiner*—Leslie Wong
(74) *Attorney, Agent, or Firm*—Oblon, Spivak, McClelland, Maier & Neustadt, P.C.

(57) ABSTRACT

Herein is disclosed a flavor precursor composition comprising as an active ingredient a flavor precursor compound (flavor precursor compound A) in which a volatile flavor compound having a mercapto group in the molecule and a non-volatile compound having a mercapto group in the molecule are bound to form a disulfide structure, or a flavor precursor compound (flavor precursor compound B) which is an organic compound represented by Formula (1) shown below in which $R^1H$ is a non-volatile compound and $R^2H$ is a volatile compound having in the molecule a furan ring structure (including a structure where part or all of the carbon—carbon double bonds thereof are hydrogenated) or a thiophene ring structure (including a structure where part or all of the carbon—carbon double bonds thereof are hydrogenated), said Formula (1) being:

$$R^1-(S)_n-R^2 \qquad (1)$$

which composition can preserve, and release, the flavor effectively and can be used in the fields of fragrances and foods.

19 Claims, 3 Drawing Sheets

FLAVOR PRECURSOR COMPOSITION AND METHOD FOR RELEASING THE FLAVOR COMPONENT

This application is a National Stage filing of PCT/JP00/02179 filed Apr. 4, 2000.

TECHNICAL FIELD

The present invention relates to a method for preserving latently the flavor of products in the fields of fragrances and foods for a prolonged period and for releasing the said flavor at a desired level only when desired, and to novel sulfide compounds capable of being an effective flavor precursor in such method.

BACKGROUND ART

A large number of studies have been made on the method for preserving, and controlling the release of, a flavor ("Latest food flavor technology", published by INDUSTRIAL TECHNOLOGY SOCIETY, 1988), and microencapsulation, enclosure in matrix, inclusion with a cyclodextrin or equivalent, as well as reaction of an enzyme upon a volatile component precursor such as a glycoside.

It is difficult, however, to control the release level as desired in a physical preserving method, and in a method employing a glycoside, the target compounds are limited to terpene alcohols and the enzyme may be inactivated when used in a heated system, these being some examples of the problems associated with the prior art.

On the other hand, mercapto group-containing compounds generally have a low flavor threshold, and frequently play an important role in the flavor characteristics of products such as fragrances and foods. For example, mercapto compounds which are furan derivatives are known as contributing greatly to the food flavor of a product such as coffee or meat. Nevertheless, since such mercapto compounds involve difficulties in controlling the flavor release level within an appropriate range because of their low flavor threshold and also in preserving the concentration thereof within a certain range for a prolonged period, a method for preserving and releasing their flavor efficiently have been demanded to be developed.

DISCLOSURE OF THE INVENTION

Under the circumstances of the prior art described above, it is an object of the present invention to provide an excellent method for preserving and releasing the flavor effectively which can be used in the fields of fragrances and foods, as well as to provide an excellent flavor precursor (novel sulfide compounds) capable of preserving and releasing the flavor effectively which can be used in the fields of fragrances and foods.

The present inventors have made an effort to accomplish the object described above and finally found that, by reacting a mercapto group-containing volatile flavor compound (for example, methanethiol, propanethiol, FMT(2-furylmethanethiol), MFT (2-methyl-3-furanthiol) or the like) with a mercapto group-containing non-volatile compound such as cysteine, homocysteine, glutathione, a cysteine-containing peptide, a mercapto group-containing synthetic polymer or the like, to produce the corresponding disulfide form, the volatile flavor compound described above can be imparted with a non-volatile nature which, in turn, allows the volatile flavor compound to be preserved stably for a prolonged period (flavor component preservation), and that a volatile flavor compound once imparted with such non-volatile nature as described above can effect, when desired, the release of the flavor component (the original volatile flavor compound) by cleavage of the S—S bond (disulfide bond) (release of the flavor component), and that, by controlling the cleavage conditions, the release level of the flavor component can be controlled.

In other words, they have found that, by converting a volatile flavor component compound into the form of a non-volatile compound by means of allowing the former compound to react with another non-volatile compound, the flavor component becomes non-volatile and becomes capable of being preserved stably for a prolonged period, and that the flavor component can be, when desired, released by an easy cleavage of the bond, and that, by altering the conditions, the released amount level of the flavor component can be controlled and the flavor can be released stably over a prolonged period, and on the basis of these findings, established the present invention (referred to as the first embodiment of the present invention).

Accordingly, the first embodiment of the present invention relates to a flavor precursor composition comprising as the active ingredient a flavor precursor compound in which a volatile flavor compound having a mercapto group in the molecule and a non-volatile compound having a mercapto group in the molecule are bound to form a disulfide structure, and to a method for releasing the flavor component from the flavor precursor composition set forth above by cleaving in various ways the disulfide bond of the flavor precursor compound comprised in the flavor precursor compositions.

The present inventors have made a further effort to accomplish the object described above and found that, by binding chemically the mercapto group of a volatile flavor compound which is a mercapto group-containing furan derivative, such as FMT(2-furylmethanethiol), MFT (2-methyl-3-furanthiol) or the like, to a non-volatile compound, the volatile flavor compound described above can be imparted with a non-volatile nature which can be preserved stably for a prolonged period, that a volatile flavor compound once imparted with such non-volatile nature as described above can effect, when desired, the release of the flavor component (the original volatile flavor compound) by reductive or thermal cleavage of the C—S or S—S bond, and that, by controlling the cleavage conditions, the released amount level of the flavor component can be controlled.

In other words, they have found that, by converting a volatile flavor component compound into the form of a compound according to the present invention, the flavor component becomes non-volatile and becomes capable of being preserved stably for a prolonged period, that the flavor component can be, when desired, released by an easy cleavage of the bond between the both component compounds, and that, by altering the conditions, the released amount level of the flavor component can be controlled and the flavor can be released stably over a prolonged period, and on the basis of these findings, established the present invention (referred to as the second embodiment of the present invention).

Accordingly, the second embodiment of the present invention relates to a novel sulfide compound which is an organic compound represented by Formula (2) shown below in which $R^1H$ is a non-volatile compound and $R^2H$ is a volatile compound having in the molecule a furan ring structure (including a structure where part or all of the carbon—carbon double bonds thereof are hydrogenated) or a thiophene ring structure (including a structure where part or all of the carbon—carbon double bonds thereof are hydrogenated), said Formula (2) being:

$$R^1-(S)_m-R^2 \quad (2)$$

wherein m represents an integer of 1 to 3, $R^1H$ represents an organic compound having a structure in which the functional group $R^1$ is bound to a hydrogen atom and $R^2H$ represents an organic compound having a structure in which the functional group $R^2$ is bound to a hydrogen atom.

In this connection, the sulfides of the present invention having the structure of a volatile flavor compound which has been imparted with a non-volatile nature are novel compounds, and include monosulfides (when m=1), disulfides (when m=2), and trisulfides (when m=3).

Among the compounds represented by Formula (2) in the second embodiment of the invention, those in which m is 2 overlap with the flavor precursor compounds of the first embodiment of the present invention described above.

The present invention will be further described below, being subdivided into the first embodiment and the second embodiment, and detailed in this order. In this connection, the first and second embodiments of the present invention together constitute a group of the inventions so linked as to form a single general inventive concept.

The first embodiment of the present invention will first be described below.

The volatile flavor compounds imparted with a nonvolatile nature (flavor component) which constitute a flavor precursor compound contained as an active ingredient in the flavor precursor composition of the present invention are grouped broadly into volatile compounds having in the molecule a furan ring structure and a mercapto group (flavor-presenting furans) and volatile compounds having no furan ring structure but having a mercapto group (flavor-presenting non-furans). As flavor-presenting furans, there may be mentioned FMT and MFT exemplified above. As flavor-presenting non-furans, there may be mentioned methanethiol, propanethiol and the like.

As non-volatile compounds with which a flavor-presenting furan or a flavor-presenting non-furan is reacted to be imparted with a non-volatile nature, there may be mentioned, for example, mercapto group-containing non-volatile compounds. Such compounds can be for example sulfur-containing amino acids and peptides such as cysteine, homocysteine, glutathione, γ-glutamylcysteine, cysteinylglycine and the like. In this case, each of these compounds binds to a flavor component compound via an S—S bond (disulfide bond).

Incidentally, it is to be noted that there have been known no compounds in the form in which a flavor-presenting furan is imparted with a non-volatile nature by using a non-volatile compound having a mercapto group via a disulfide fond, as exemplified above. On the other hand, there have been indeed known several compounds in the form in which a flavor-presenting non-furan is imparted with a non-volatile nature, but none of them have been known as having an use as a flavor precursor compound such as the one according to the present invention.

A compound of the present invention obtained by imparting a flavor-presenting furan with a non-volatile nature may be for example produced by reacting a nonvolatile disulfide compound with a flavor-presenting furan in an alkali solution.

Next, ways of preparing a flavor precursor composition of the present invention will be described. There are no particular limitations thereon, and a flavor precursor compound according to the present invention alone or, together with an appropriate excipient, may be formulated into a suitable form such as powder, granule, liquid and paste. A flavor precursor compound per se of the present invention, when used as a flavor precursor, is encompassed in the flavor precursor composition of the present invention (in a broad sense), in view of its application.

Finally, a method for using a flavor precursor composition of the present invention will be described. An essential point of the method involves cleaving the disulfide bond between the volatile flavor component compound constituting a flavor precursor compound comprised in a flavor precursor composition of the present invention and the non-volatile compound.

As an example of the method, there is one wherein the disulfide bond is cleaved using a reducing compound (e.g., sodium boron hydride). Specifically, a flavor precursor composition is, when desired, added with a reducing compound, whereby the disulfide bond can be cleaved.

As another example of the method, there is one wherein the disulfide bond is cleaved using a compound exerting its reducing ability via a reversible reaction (e.g., glucose). Specifically, a flavor precursor composition is added with a compound which exerts its reducing ability, and the resultant mixture is, when desired, placed under the conditions where the compound can express its reducing ability (e.g., heating and altering the pH), whereby the disulfide bond can be cleaved.

As still another example of the method, there is one wherein the disulfide bond is cleaved using a compound having a free mercapto group (e.g., cysteine). In greater detail, a flavor precursor composition is, when desired, is added with a compound having a free mercapto group, whereby the disulfide bond can be cleaved.

Furthermore, that can be done by heating. This is done by merely heating a fragrance or food which has been added with a flavor precursor composition of the present invention.

Still furthermore, that can be done by altering the pH. E.g., a flavor precursor composition is, when desired, raised in pH value with an alkali or the like, whereby part of the disulfide bonds can be cleaved.

Or, that can be done by an electric reducing action. In greater detail, a flavor precursor composition is, when desired, placed under an electrically negative condition, whereby the disulfide bond can be cleaved.

And, control of the released amount of the flavor component can be effected, e.g., by controlling the amount to be added, of a reducing compound, by controlling the heating conditions, by controlling the change in pH value, by controlling the electrical current, or the like.

The second embodiment of the present invention will be described below.

A volatile flavor compound (flavor component) to be imparted with a non-volatile nature according to the invention is a volatile compound having in the molecule both a furan ring structure and a mercapto group (flavor-presenting furan). As such compounds, there can be mentioned for example FMT and MFT mentioned above.

A non-volatile compound with which a flavor-presenting furan is reacted to be imparted with a nonvolatile nature can be for example an amino acid such as alanine. In this case, each of these compounds is bound to a flavor component compound via a C—S bond (sulfide bond).

Another example of a non-volatile compound is a non-volatile compound having a mercapto group. As such compounds, there can be mentioned for example sulfur-containing amino acids and peptides such as cysteine, homocysteine, glutathione, γ-glutamylcysteine, cysteinylglycine and the like. In this case, each of these compounds binds to a flavor component compound via an S—S bond (disulfide bond).

Still another example of a non-volatile compound is a disulfide bond-containing amino acid or peptide. As such compounds, there can be mentioned for example cystine. In this case, each of these compounds is bound to a flavor component compound via an S—S—S bond (trisulfide bond).

Various sulfide compounds of the present invention described above can be synthesized, specifically by the following procedures;

First, a monosulfide compound can be obtained by reacting a halogenated non-volatile compound with a volatile thiol compound in an alkali/methanol or an aqueous alkali solution.

Second, a disulfide compound can be obtained by binding a non-volatile thiol compound with a volatile thiol compound oxidatively in the presence of oxygen in an alkali solution. Alternatively, it can be obtained by reacting a non-volatile disulfide compound with a volatile thiol compound in an alkali solution.

Finally, a trisulfide compound can be obtained by a disproportionation of a disulfide compound described above in the presence of $CuCl_2$.

The present invention has been described above on the assumption that the compound represented by Formula (2) is one in which $R^2H$ is a volatile compound having a furan ring structure in the molecule. However, a furan ring readily undergoes a conversion into a hydrogenated structure in which part or all of the C—C double bonds are hydrogenated, and the resulting volatile compound containing such structure in the molecule can behave similarly to a furan ring-containing volatile compound insofar as a flavor precursor compound of the present invention is concerned. A volatile compound having a thiophene ring structure in which the oxygen atom in a furan ring is replaced with a sulfur atom, and the volatile compound having a structure in which part or all of the C—C double bonds in the thiophene ring are hydrogenated also behave similarly to a furan ring-containing volatile compound for the purpose of a flavor precursor compound of the present invention. Accordingly, a volatile compound represented by $R^2H$ in the general Formula (2) includes a volatile compound having a structure in which part or all of the double bonds in the furan ring are hydrogenated as well as one having a thiophene ring structure or a structure in which part or all of the double bonds in the thiophene ring are hydrogenated as described above.

Incidentally, as examples of the structure having a furan ring which, in turn, constitute a sulfide, there can be mentioned functional groups such as 2-Furfuryl, 2-Methyl-3-furyl, 5-Methyl-2-furfuryl, 3-Furyl, 1-(2-Furyl)ethyl, 1-(2-Methyl-3-furylthio)ethyl, 2-Furyl and hydrogenated forms thereof, and as examples of the structure having a thiophene ring, there can be mentioned functional groups such as 2-Thenyl, 2-Methyl-3-thienyl, 5-Methyl-2-thenyl, 3-Thienyl, 1-(2-Thienyl)ethyl, 1-(2-Methyl-3-thienylthio)ethyl, 2-Thienyl and hydrogenated forms thereof.

Next, a method for using a sulfide compound according to the present invention will be described. An essential point of the method involves a reductive or thermal cleavage of the bond between the volatile flavor component compound and the non-volatile compound which are the constituents of the compound of the present invention. Specifically, a reductive cleavage can be for example accomplished using an electric reducing device. A thermal cleavage can be for example accomplished by means of a simple heating of a fragrance or a food in which a compound according to the present invention has been incorporated.

Controlling the released amount level of the flavor component by altering the conditions can be for example accomplished as follows. I.e., the controlling can be effected by altering the current and the current sending time period in the case of electric reduction, and by altering the heating temperature and heating time period in the case of thermal cleavage.

Finally, distribution of a novel sulfide compound of the present invention will be described. The compound may be distributed as a flavor precursor compound per se or as a flavor precursor composition containing the compound as an active ingredient.

The form during distribution is not particularly limited and can be of a pure material or in an appropriate formulation with an appropriate excipient such as powder, granule, liquid and paste.

BEST MODE FOR CARRYING OUT THE INVENTION

Figure 1:
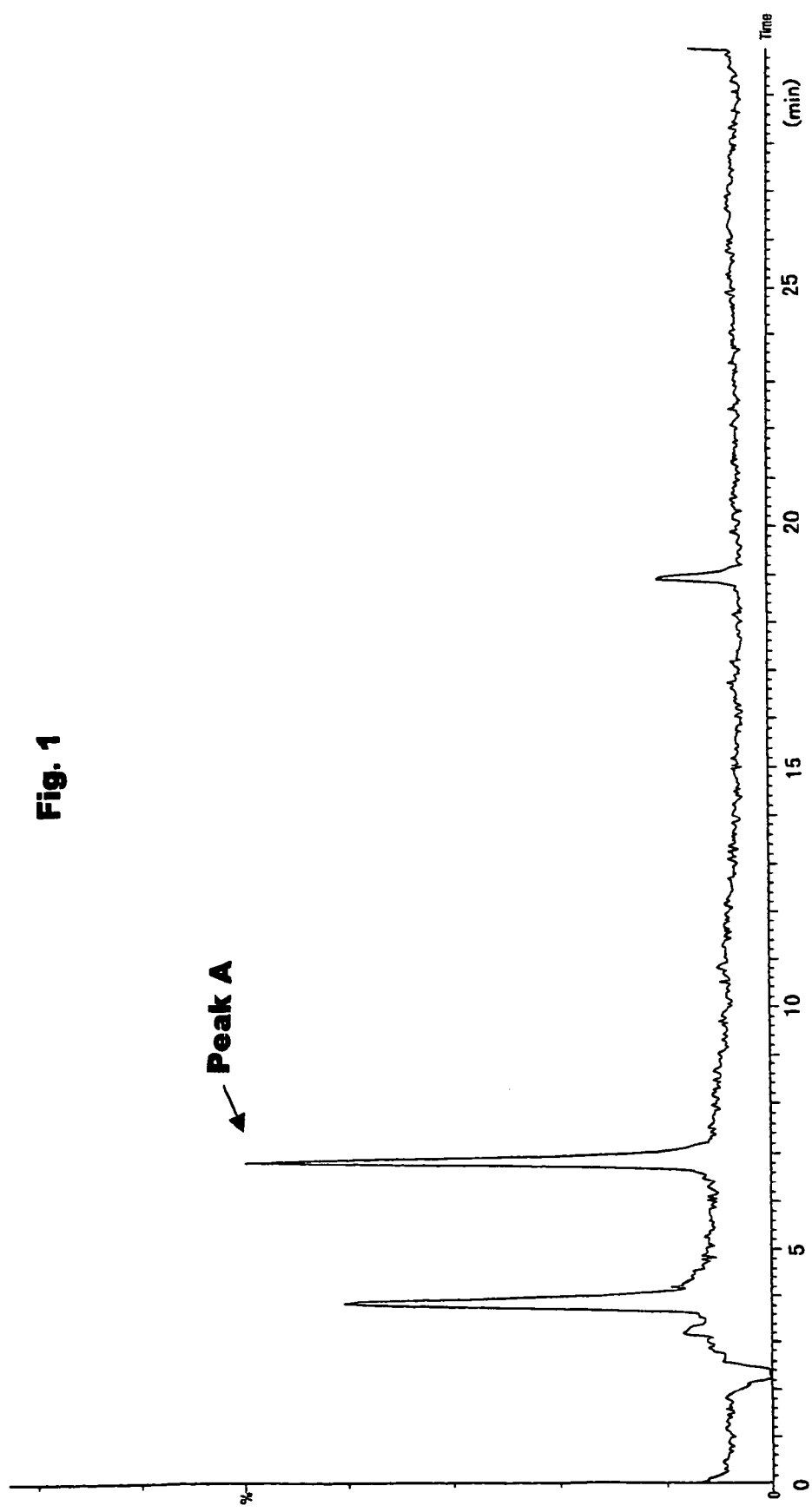
FIG. 1 shows a chromatogram of a reaction mixture containing a compound of the present invention (Example 4).

The present invention will be further described with reference to the following examples which are not intended to restrict the invention, and the variation and the modification of the present invention without departing the gist described above and below are all included in the present invention.

EXAMPLE 1

Synthesis of Cys-MFT 100 mg of cystine was dissolved in 50 ml of an aqueous 0.1 N solution of sodium hydroxide. The resulting solution was combined with 10 ml of a methanol solution containing 40 mg of MFT (2-methyl-3-furanthiol), and the mixture was stirred for reaction under a nitrogen atmosphere at room temperature for 5 days.

After the reaction, the reaction solution was neutralized to pH 7 and washed twice with 50 ml of ether (100 ml in total), and then the aqueous layer was concentrated to dryness using a rotary evaporator. The concentrate thus obtained was dissolved in 10 ml of distilled water and applied onto a solid phase extraction column (BONDELUTE C18, 5.0 g packing, ex VARIAN) to adsorb the target compound. The solid phase extraction column was washed twice with 20 ml of distilled water (40 ml in total), and then the adsorbed component was eluted with 20 ml of methanol. The resulting methanol solution thus obtained was frozen rapidly using liquid nitrogen and dried in vacuo to obtain 10.3 mg of Cys-MFT (cysteine 2-methyl-3-furanthiol disulfide, i.e., S-(2-methyl-3-furylthio)-L-cysteine) as a white powder.

EXAMPLE 2

Synthesis of Cys-FMT

Example 1 was repeated except that 40 mg of FMT (2-furylmethanethiol) was used instead of the MFT, to obtain 12.5 mg of Cys-FMT (cysteine 2-furylmethanethiol disulfide, i.e., S-(2-furfurylthio)-L-cysteine) as a white powder.

EXAMPLE 3

Synthesis of GSH-MFT

Example 1 was repeated except that 300 mg of oxidized-form glutathione was used instead of the cystine, to obtain 18.9 mg as a white powder.

EXAMPLE 4

Synthesis of S-(3-Furyl)-L-cysteine 1.86 g (15.4 mmol) of L-cysteine (ex AJINOMOTO) was suspended in 15 ml of distilled water and stirred on an ice bath with bubbling with nitrogen. After 30 minutes, 0.68 g (17 mmol) of sodium hydroxide was added, resulting in a uniform dissolution of the L-cysteine. After the complete dissolution of the sodium hydroxide, 2.5 g (17 mmol) of 3-bromofuran (ex Aldrich) was added thereto and stirred at room temperature for 5 hours. After the reaction, 6N hydrochloric acid was added to adjust the solution to pH 2.0. After a trace amount of a precipitate and the unreacted 3-buromofuran were removed by decanting from the reaction mixture, the mixture was applied onto an ODS solid phase extraction column (ex VARIANT) to remove any colored substances.

A method for separating the target product S-(3-furyl)-L-cysteine from the reaction solution from which the colored substances had been removed was then studied. The reaction solution obtained was subjected to separation by HPLC under the following conditions: "Capcell Pak C-18" (inner diameter: 2.0 mm, and length: 150 mm, ex SHISEIDO) being employed as the column, the column temperature being 40° C., the eluting solution being an acetonitle/water mixture, used with a gradient from 5 to 50% acetonitrile in water over an initial 20 minutes at a flow rate of 0.2 ml/min, and the detection being carried out by ESI-MS having a detection ion mass range of 100 to 500, which gave the chromatogram shown in FIG. 1.

Figure 2:
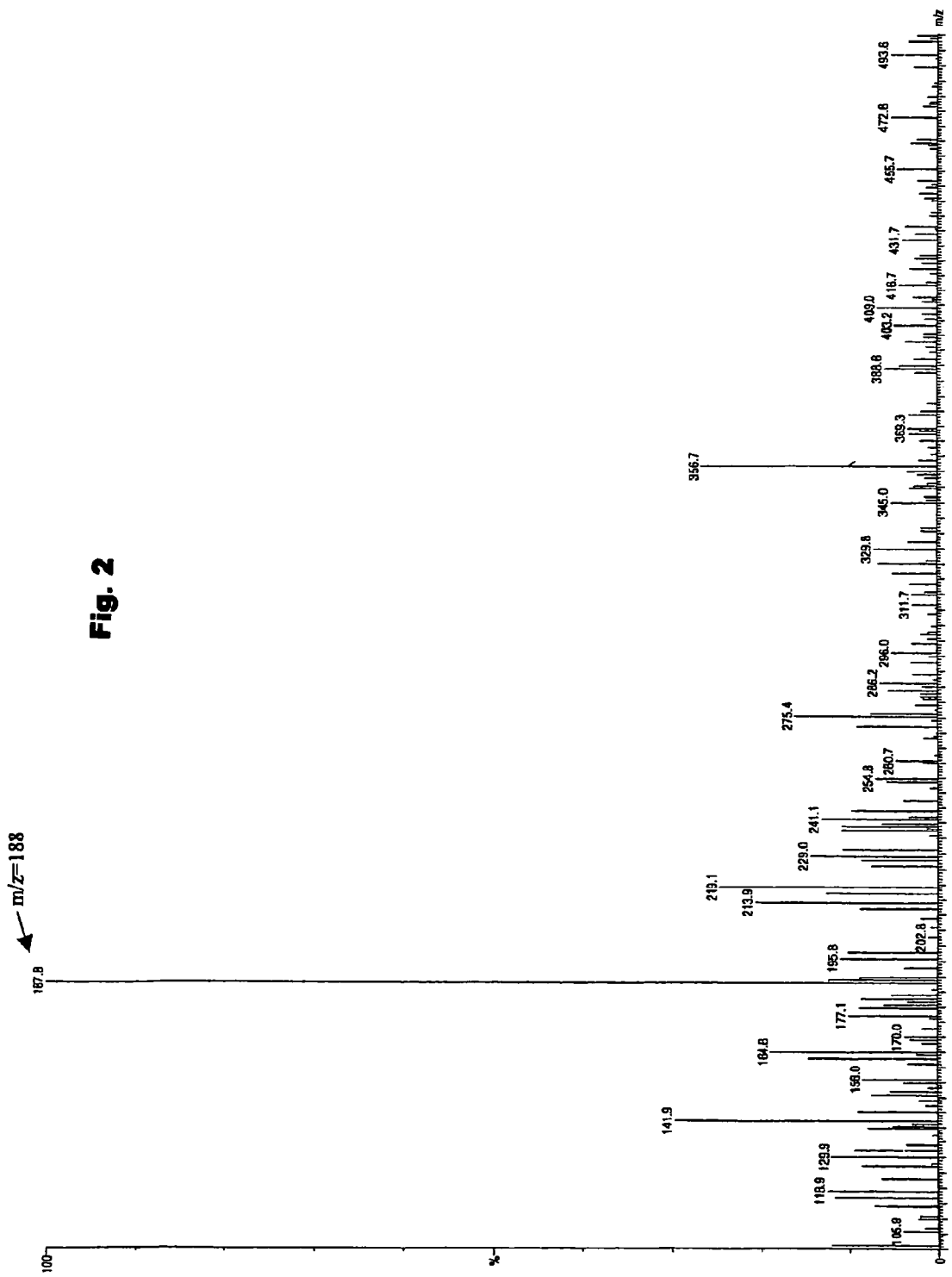
FIG. 2 shows an ESI-MS spectrum of the component corresponding to Peak A in FIG. 1 (Example 4).

The ESI-MS (Electron Spray Ionization-Mass Spectrometry) spectra of the component corresponding to Peak A in FIG. 1 were measured, and the results revealed the presence of a m/z=188 fragment which corresponded to MH$^+$ of the target component as shown in FIG. 2.

EXAMPLE 5

Use in Consommé Soup (1)

A commercially available solid beef consommé soup was supplemented with Cys-MFT in such amount that its concentration would be 4 ppm when ingested, and dissolved in hot water to prepare a consommé soup, which was kept at 70° C. in an open system, and then compared with a non-supplemented soup. The supplemented soup (present invention) exhibited a markedly more intense beef broth-like flavor when compared with the non-supplemented soup (control).

Another soup supplemented in the similar manner, but only with MFT in an amount giving a 0.2 ppm concentration upon ingestion (control), exhibited a more intense flavor than the Cys-MFT-supplemented soup immediately after supplementation, but subsequently it became weakened in flavor rapidly as the time elapsed to a level lower than that in the Cys-MFT-supplemented soup (present invention) after 10 minutes.

EXAMPLE 6

Use in Instant Coffee

A commercially available (freeze-dried) instant coffee was added with Cys-FMT in such amount that its concentration would be 1 ppm when ingested, and then with hot water to prepare a coffee, which was kept at 70° C. in an open system and then compared with a non-added coffee. The added coffee (present invention) exhibited a markedly more intense freshly-brewed coffee-like flavor when compared with the non-added coffee (control).

Another coffee added in the similar manner, but only with FMT in an amount giving a 0.05 ppm concentration upon ingestion (control), exhibited a more intense flavor than the Cys-FMT-added coffee (present invention) immediately after addition, but subsequently it became weakened in flavor rapidly as the time elapsed to a level lower than that in the Cys-FMT-added coffee after 10 minutes.

EXAMPLE 7

Use in Consommé Soup (2)

A commercially available solid beef consommé soup was supplemented with GSH-MFT in such amount that its concentration would be 8 ppm when ingested, and dissolved in hot water to prepare a consommé soup, which was kept at 70° C. in an open system, and then compared with a non-supplemented soup. The supplemented soup (present invention) exhibited a markedly more intense beef broth-like flavor when compared with the non-supplemented soup (control).

Another soup supplemented in the similar manner, but only with MFT in an amount giving a 0.2 ppm concentration upon ingestion (control), exhibited a more intense flavor than the GSH-MFT-supplemented soup (present invention) immediately after supplementation, but subsequently it became weakened in flavor rapidly as the time elapsed to a level lower than that in the GSH-MFT-supplemented soup (present invention) after 10 minutes.

EXAMPLE 8

Release of the Flavor Component Using an Electric Reducing Device

Figure 3:
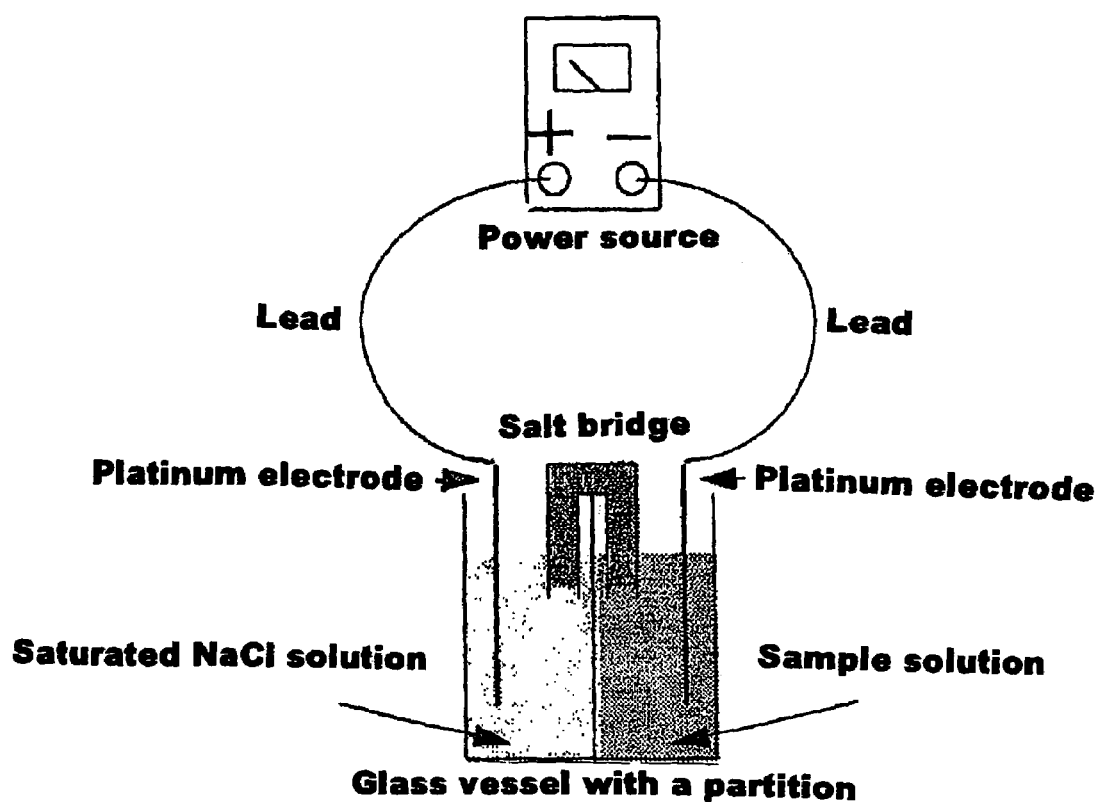
FIG. 3 shows a conceptual exemplification of an electric reducing device capable of being used for releasing the flavor component from a flavor precursor compound of the present invention.

An aqueous 0.1% solution of Cys-FMT was placed in an electric reducing device exemplified in FIG. 3, which was connected to a constant current power supply. By passing a 2 mA electric current through this device, the Cys-FMT was reduced electrically to generate FMT, resulting in a coffee-like flavor. By turning off the current, the generation of FMT was terminated, indicating the possibility of controlling the level of the flavor component generated.

The release of a flavor in this manner can be utilized, for example, for fragrance products at shops and offices or for a domestic use.

INDUSTRIAL APPLICABILITY

According to the present invention, the flavor of a product in the fields of fragrances and foods can readily be preserved for a prolonged period latently and such flavor can be released at a desired level only when desired.

The invention claimed is:

1. A flavor precursor composition comprising as an active ingredient
a flavor precursor compound which is an organic compound represented by Formula (1):

$$R^1-(S)_n-R^2 \qquad (1)$$

wherein n is 2, $R^2$ is selected from the group consisting of 2-Furfuryl, 2-Methyl-3-furyl, 5-Methyl-2-furfuryl, 3-Furyl, 1-(2-Furyl)ethyl, 1-(2-Methyl-3-furylthio)ethyl, 2-Furyl, 2-Thenyl, 2-Methyl-3-thienyl, 5-Methyl-2-thenyl, 3-Thienyl, 1-(2-Thienyl)ethyl, 1-(2-Methyl-3-thienylthio)ethyl, 2-Thienyl and hydrogenated forms thereof and $R^1$ represents the residue of a sulfur-containing amino acid or peptide selected from the group consisting of cysteine, homocysteine, glutathione, γ-glutamylcysteine, and cysteinylglycine wherein the mercapto group of said sulfur-containing amino acid or peptide is present in the disulfide bond of the organic compound represented by Formula (1).

2. A method for releasing the flavor component from the flavor precursor composition as set forth in claim 1 wherein the disulfide bond in said flavor precursor compound is cleaved using a reducing compound.

3. A method for releasing the flavor component from the flavor precursor composition as set forth in claim 1 wherein the disulfide bond in said flavor precursor compound is cleaved using a compound exerting its reducing ability via a reversible reaction.

4. A method for releasing the flavor component from the flavor precursor composition as set forth in claim 1 wherein the disulfide bond in said flavor precursor compound is cleaved using a compound having a free mercapto group.

5. A method for releasing the flavor component from the flavor precursor composition as set forth in claim 1 wherein the disulfide bond in said flavor precursor compound is cleaved by heating.

6. A method for releasing the flavor component from the flavor precursor composition as set forth in claim 1 wherein the disulfide bond in said flavor precursor compound is cleaved by altering the pH.

7. A method for releasing the flavor component from the flavor precursor composition as set forth in claim 1 wherein the disulfide bond in said flavor precursor compound is cleaved by an electric reducing action.

8. A novel sulfide compound which is an organic compound represented by Formula (2):

$$R^1-(S)_m-R^2 \qquad (2)$$

wherein m represents an integer of 2 or 3, $R^2$ is selected from the group consisting of 2-Furfuryl, 2-Methyl-3-furyl, 5-Methyl-2-furfuryl, 3-Furyl, 1-(2-Furyl)ethyl, 1-(2-Methyl-3-furylthio)ethyl, 2-Furyl, 2-Thenyl, 2-Methyl-3-thienyl, 5-Methyl-2-thenyl, 3-Thienyl, 1-(2-Thienyl)ethyl, 1-(2-Methyl-3-thienylthio)ethyl, 2-Thienyl and hydrogenated forms thereof and $R^1$ represents the residue of a sulfur-containing amino acid or peptide selected from the group consisting of cysteine, homocysteine, glutathione, γ-glutamylcysteine, and cysteinylglycine wherein the mercapto group of said sulfur-containing amino acid or peptide is present in the disulfide or trisulfide bond of the organic compound represented by Formula (2),
or
a novel compound which is an organic compound represented by Formula (3):

$$R^3-S-R^4 \qquad (3)$$

wherein $R^4$ is selected from the group consisting of 2-Methyl-3-furyl, 5-Methyl-2-furfuryl, 3-Furyl, 1-(2-Furyl)ethyl, 1-(2-Methyl-3-furylthio)ethyl, 2-Furyl, 2-Methyl-3-thienyl, 5-Methyl-2-thenyl, 3-Thienyl, 1-(2-Thienyl)ethyl, 1-(2-Methyl-3-thienylthio)ethyl, 2-Thienyl and hydrogenated forms thereof and $R^3$ represents the residue of a sulfur-containing amino acid or peptide selected from the group consisting of cysteine homocysteine, glutathione, γ-glutamylcysteine, and cysteinylglycine wherein the mercapto group of said sulfur-containing amino acid or peptide is present in the monosulfide bond of the organic compound represented by Formula (3).

9. A food or drink comprising a flavor precursor composition of claim 1.

10. A food or drink comprising the sulfide compound of claim 8.

11. A flavor precursor composition comprising as an active ingredient the sulfide compound of claim 8
and a suitable excipient.

12. A method for releasing the flavor component from the flavor precursor composition as set forth in claim 11 wherein the sulfide bond in said flavor precursor is cleaved using a reducing compound.

13. A method for releasing the flavor component from the flavor precursor composition as set forth in claim 11 wherein the sulfide bond in said flavor precursor is cleaved using a compound exerting its reducing ability via a reversible reaction.

14. A method for releasing the flavor component from the flavor precursor composition as set forth in claim 11 wherein the sulfide bond in said flavor precursor is cleaved using a compound having a free mercapto group.

15. A method for releasing the flavor component from the flavor precursor composition as set forth in claim 11 wherein the sulfide bond in said flavor precursor is cleaved by heating.

16. A method for releasing the flavor component from the flavor precursor composition as set forth in claim 11 wherein the sulfide bond in said flavor precursor is cleaved by altering the pH.

17. A method for releasing the flavor component from the flavor precursor composition as set forth in claim 11 wherein the sulfide bond in said flavor precursor is cleaved by an electric reducing action.

18. A food or drink comprising a flavor precursor composition of claim 11.

19. The flavor precursor composition of claim 1, further comprising a suitable excipient.

* * * * *

UNITED STATES PATENT AND TRADEMARK OFFICE
CERTIFICATE OF CORRECTION

PATENT NO. : 7,011,860 B1
APPLICATION NO. : 09/926180
DATED : March 14, 2006
INVENTOR(S) : Hidehiko Wakabayashi et al.

It is certified that error appears in the above-identified patent and that said Letters Patent is hereby corrected as shown below:

Column 10, line 22, "cysteine homocysteine," should read -- cysteine, homocysteine, --.

Signed and Sealed this

Twenty-seventh Day of March, 2007

JON W. DUDAS
*Director of the United States Patent and Trademark Office*